US008612006B2

(12) United States Patent
Lozano et al.

(10) Patent No.: US 8,612,006 B2
(45) Date of Patent: *Dec. 17, 2013

(54) INDUCING NEUROGENESIS WITHIN A HUMAN BRAIN

(75) Inventors: Andres M. Lozano, Toronto (CA); Hiroki Toda, Kyoto (JP)

(73) Assignee: Functional Neuromodulation, Toronto (CA)

( * ) Notice: Subject to any disclaimer, the term of this patent is extended or adjusted under 35 U.S.C. 154(b) by 88 days.

This patent is subject to a terminal disclaimer.

(21) Appl. No.: 11/303,292

(22) Filed: Dec. 16, 2005

(65) Prior Publication Data

US 2007/0067001 A1   Mar. 22, 2007

Related U.S. Application Data

(60) Provisional application No. 60/636,979, filed on Dec. 17, 2004.

(51) Int. Cl.
*A61N 1/18* (2006.01)

(52) U.S. Cl.
USPC ............................................. 607/45; 607/2

(58) Field of Classification Search
USPC ............... 607/2, 3, 45, 115, 116, 120, 139
See application file for complete search history.

(56) References Cited

U.S. PATENT DOCUMENTS

| 5,119,832 | A | * | 6/1992 | Xavier | 607/117 |
|---|---|---|---|---|---|
| 5,423,877 | A | * | 6/1995 | Mackey | 607/117 |
| 5,683,422 | A | | 11/1997 | Rise | |
| 5,707,396 | A | | 1/1998 | Benabid | |
| 5,792,186 | A | * | 8/1998 | Rise | 607/2 |
| 6,066,163 | A | * | 5/2000 | John | 607/45 |
| 6,094,598 | A | * | 7/2000 | Elsberry et al. | 607/116 |
| 6,128,537 | A | * | 10/2000 | Rise | 607/45 |
| 6,167,311 | A | * | 12/2000 | Rezai | 607/45 |
| 7,003,352 | B1 | * | 2/2006 | Whitehurst | 607/45 |
| 8,346,365 | B2 | * | 1/2013 | Lozano | 607/45 |
| 2002/0091419 | A1 | * | 7/2002 | Firlik et al. | 607/45 |
| 2005/0010262 | A1 | * | 1/2005 | Rezai et al. | 607/46 |
| 2005/0119712 | A1 | | 6/2005 | Shafer | |

* cited by examiner

*Primary Examiner* — Carl H Layno
*Assistant Examiner* — Jennifer Ghand
(74) *Attorney, Agent, or Firm* — Wilson, Sonsini, Goodrich & Rosati

(57) ABSTRACT

Methods and apparatus for inducing neurogenesis within a human. An implantable signal generator is used to deliver high frequency stimulation to deep brain tissue elements. The implanted device delivers treatment therapy to the brain to thereby induce neurogenesis by the human. A sensor may be used to detect various symptoms of nervous system discovery. A microprocessor algorithm may then analyze the output from the sensor to regulate the stimulation and/or drug therapy delivered to the brain.

18 Claims, 5 Drawing Sheets

INDUCING NEUROGENESIS WITHIN A HUMAN BRAIN

This patent application claims priority to U.S. Provisional Application Ser. No. 60/636,979 filed Dec. 17, 2004, which is incorporated herein by reference in its entirety.

FIELD OF THE INVENTION

The present invention relates to techniques for providing treatment therapy to induce neurogenesis within a brain of a human by way of high-frequency brain stimulation and/or drug infusion.

BACKGROUND OF THE INVENTION

It has generally been believed that loss of neurons in the adult human brain—as it occurs in aging humans and in neurological disorders—is an irreversible process. Many major diseases of the human brain involve deficiencies of select neuronal populations. The inability by the adult human brain to generate replacement cells is thought to be a leading cause for the irreversible and progressive nature of several neurological diseases and is responsible for persistent and ongoing impairment. In most regions of the human brain, the generation of neurons is generally confined to a discrete developmental period. After this developmental period, it believed that no further generation of brain cells occurs in the living human brain.

Exceptions to this general rule exist in specific regions of the adult mammalian brain. The dentate gyrus of the hippocampus and the subventricular zone have been shown to generate new neurons well into the postnatal and adult period. For example, in the rodent brain, granule neurons may be generated throughout life from a population of continuously dividing progenitor cells residing in the subgranular zone of the dentate gyrus. It is likely that the human brain may also enjoy these regenerative features.

Attempts have been made to learn more about possible neurogenesis in the adult human brain. For example, scientists have dissected human brain tissue from postmortem patients to achieve neurogenesis. Unfortunately, however, the genesis of new neurons in situ in the living adult human brain and methods to enhance, control or modulate this process have not yet been demonstrated. Accordingly, attempts have been made to prevent or slow down neurodegeneration of the human brain. For example, U.S. Pat. No. 5,683,422 discloses techniques for treating neurodegenerative disorders by electrical brain stimulation. Similarly, U.S. Pat. No. 5,707,396 describes methods of arresting degeneration of the neurons by high frequency stimulation.

It is therefore desirable to provide a technique for inducing neurogenesis (namely, the producing of new or replacement neurons) within a living brain of an adult human.

BRIEF SUMMARY OF THE INVENTION

An embodiment of the invention uses high frequency electrical stimulation of deep brain elements of a human to induce neurogenesis. The treatment is carried out by an implantable signal generator and at least one implantable electrode having a proximal end coupled to the signal generator and having a stimulation portion for electrically affecting deep brain tissue elements of a human. Alternatively, the treatment may be carried out by an implantable pump and at least one catheter having a proximal end coupled to the pump and having a discharge portion for infusing therapeutic dosages of the one or more drugs into a predetermined infusion site in deep brain elements. By using the foregoing techniques, neurogenesis within a human can be significantly improved. In other embodiments of the invention, drug infusion may be used as treatment therapy instead of or in addition to the electrical stimulation.

In another embodiment of the invention, a sensor is used in combination with the signal generator and stimulating electrodes to induce neurgenesis. Control means responsive to the sensor may thereby regulate the signal generator and/or pump so that the neurological disorder is treated.

By using the foregoing techniques, neurodegenerative and cognitive disorders can be controlled or treated to a degree unattainable by prior art methods or apparatus.

DETAILED DESCRIPTION OF THE INVENTION

The invention discloses techniques for delivering treatment therapy to deep brain elements of a human brain to induce neurogenesis. The applicants have discovered that neurogenesis can be induced through delivery of treatment therapy such as high frequency stimulation to deep brain elements. In one experiment, high frequency stimulation was used of the anterior thalamic nuclei to find that this surgical approach enhanced neurogenesis in rats. Accordingly, the invention incorporates electrical stimulation and/or drug infusion techniques to directly or indirectly influence tissue elements within the brain. One or more electrodes and/or catheters are implanted in the brain so that the stimulation or infusion portions lie within or in communication with predetermined portions of the brain. The electrical stimulation or drug therapy influences the deep brain elements to achieve the desired result.

These techniques of the present invention are suitable for use within any implantable medical device. In an embodiment, the present invention is implemented within an implantable neurostimulator system, however, those skilled in the art will appreciate that the present invention may be implemented generally within any implantable medical device system including, but not limited to, implantable drug delivery systems, implantable systems providing stimulation and drug delivery.

The present invention may be utilized to treat, for example, any number of conditions that exhibit neuronal loss including, but not limited to, depression, epilepsy, post cranial irradiation, steroid induced impairment in neurogenesis, stress disorders, cognitive disorders. Alzheimer's disease, mild cognitive impairment (MCI), and other neurodegenerative diseases. Such other neurodegenerative diseases include Amyotrophic lateral sclerosis (ALS), Huntingtons, Spinocerebellar ataxics (SCA's).

Figure 4A:
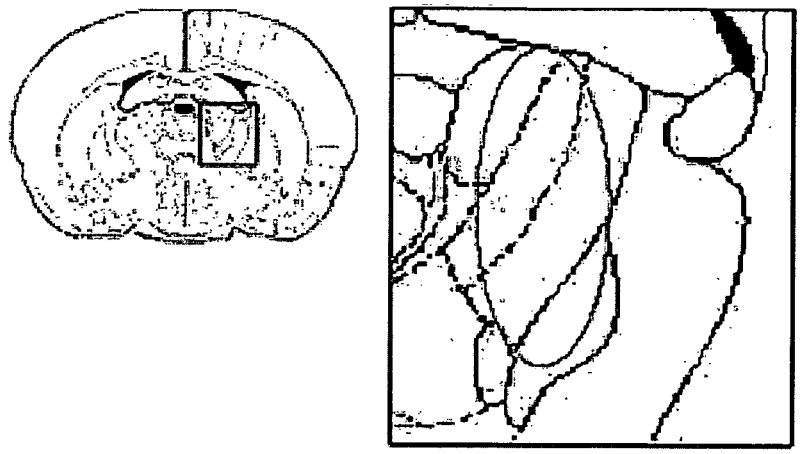
FIG. 4(a) is a diagram depicting the anterior thalamic nuclei complex and FIG. 4(b) is a diagram depicting the dentate gyrus.

The targeted treatment sites are deep brain elements of the human brain and include, for example, the anterior thalamic nuclei complex (FIG. 4(a)), the periventricular zone, the Papez circuit, and the cerebellum. The Papez circuit is generally a neuronal circuit in the limbic system, consisting of the hippocampus, fornix, mammillary body, anterior thalamic nuclei, and cingulate gyrus. Stimulation or drug therapy along the Papez circuit may lead to neurogenesis in the hippocampus. When the periventricular zone is influenced in accordance with the present invention, new neurons may migrate to the striatum, cortex, or the substantia nigra, and brainstem and therefore lead to the repopulation of neurons in such areas. The cerebellum is another brain location where increasing neurogenesis may be therapeutically desirable. In particular, the foregoing techniques may be used to reactivate neurogenesis later in life by application of electrical stimulation in either the cerebellum or cerebellar afferent or efferents. In each instance and for each target, the application of neurotrophic factors could also be used to enhance neurogenesis for therapeutic goals.

Thus, the site of stimulation may be chosen based on the neural structures that are affected by neuronal loss and which ones would benefit from enhanced neurogenesis. For example, targeting the hippocampal neuronal loss may be utilized to treat depression, epilepsy, post cranial irradiation, steroid induced impairment in neurogenesis, stress disorders, cognitive disorders and Alzheimer's disease. Targeting the cortical, striatal, substantia nigra, brainstem and cerebellar loss may be utilized to treat Huntington's Disease, Alzheimers, multiple system atrophy, Parkinson's disease, post-irradiation disorders, paraneoplastic disorders and the Spinocerebellar ataxias. The techniques of the present invention may also be applicable to treat neuronal loss that occurs as a consequence of congenital disorders, stroke, anoxia, hypoxia, hypoglycemia, metabolic disorders, head injury, drug and alcohol toxicity, nutritional deficiencies, auto-immune, infectious and inflammatory processes.

Figure 1:
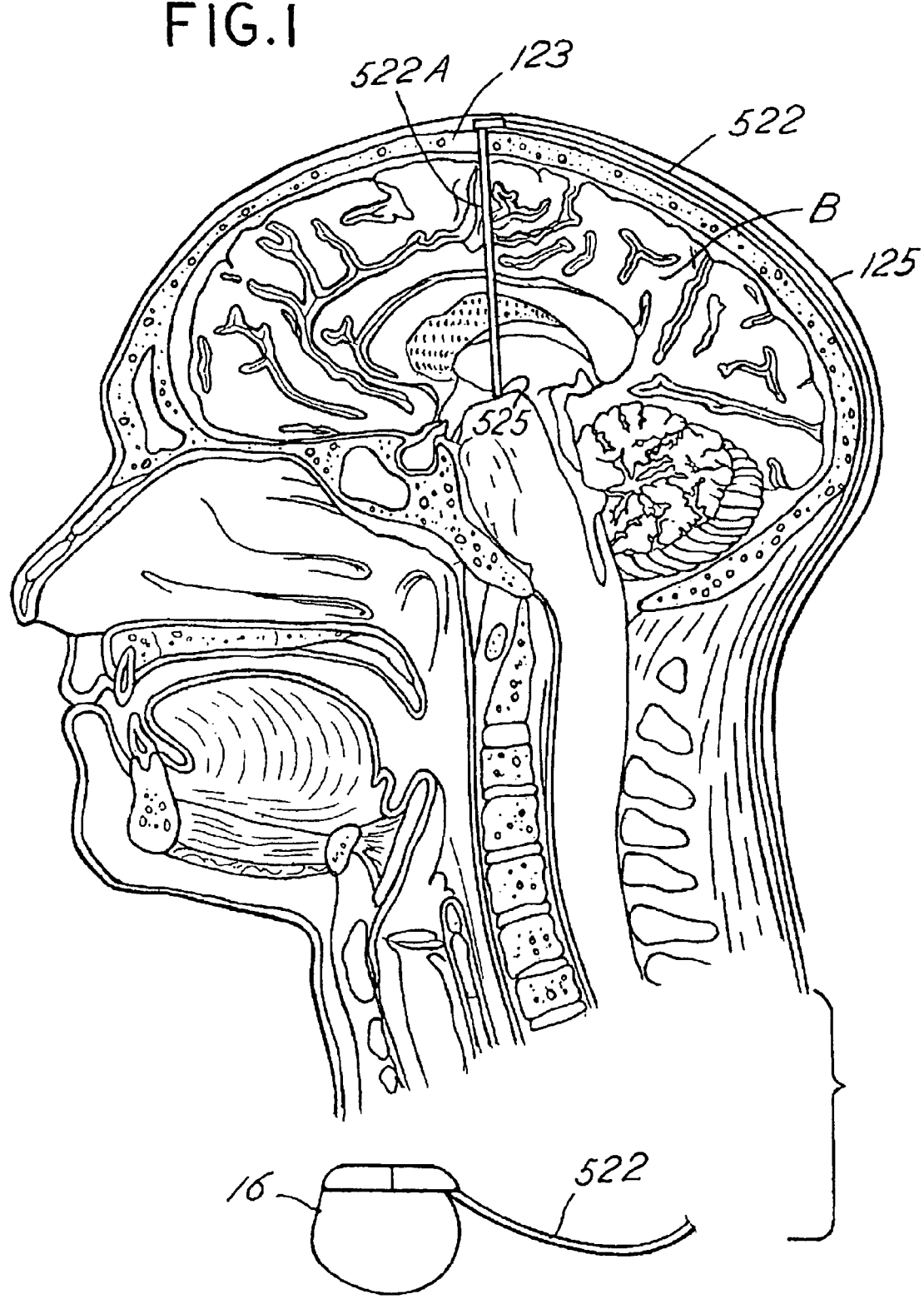
FIG. 1 is a diagrammatic illustration of an electrode implanted in a brain according to an embodiment of the present invention and a signal generator coupled to the electrode.

Referring to FIG. 1, an implantable neurostimulator device 16 made in accordance with an embodiment may be implanted below the skin of a patient. A lead 522A is positioned to stimulate a specific site 525 in a brain (B). Device 16 may take the form of a modified signal generator Model 7424 manufactured by Medtronic, Inc. under the trademark Itrel II which is incorporated by reference. Lead 522A may take the form of any of the leads sold with the Model 7424 such as Model 3387, for stimulating the brain, and is coupled to device 16 by a conventional conductor 522. One or more external programmers (not shown) may be utilized to program and/or communicate bi-directionally with the implanted device 16.

As shown, the distal end of lead 522A terminates in four stimulation electrodes implanted into a portion of the brain by conventional stereotactic surgical techniques. Each of the four electrodes is individually connected to device 16 through lead 522A and conductor 522. Lead 522A is surgically implanted through a hole in the skull 123 and conductor 522 is implanted between the skull and the scalp 125 as shown in FIG. 1. Conductor 522 is joined to implanted device 16 in the manner shown. Referring to FIG. 2A, device 16 is implanted in a human body 120 in the location shown. Body 120 includes arms 122 and 123. Alternatively, device 16 may be implanted in the abdomen. Conductor 522 may be divided into twin leads 522A and 522B that are implanted into the brain bilaterally as shown. Alternatively, lead 522B may be supplied with stimulating pulses from a separate conductor and signal generator. Leads 522A and 522B could be 1) two electrodes in two separate nuclei that potentiate each others effects or 2) nuclei with opposite effects with the stimulation being used to fine tune the response through opposing forces. It will be appreciated, however, that any number of electrodes may be implanted within the brain in accordance with the invention. Additionally, one or more secondary electrodes may be implanted so that a secondary stimulation portion lies in communication with another predetermined portion of a brain. Moreover, as will be discussed below, one or more catheters, coupled to a pump, may be implanted so that a secondary stimulation portion lies in communication with the tissue elements of the brain.

The device 16 may be operated to deliver stimulation to deep brain tissue elements to thereby induce neurogenesis within the human brain. The particular stimulation delivered may be performed by selecting amplitude, width and frequency of stimulation by the electrode. The possible stimulations include between 50 Hertz and 1000 Hertz for frequency, between 0.1 Volts and 10.0 Volts for pulse amplitude, and between 30 μSeconds and 450 μSeconds for pulse width.

The system may be utilized in monopolar, bipolar, or multipolar configurations, in an either continuous or cyclical mode, and in either an open loop or closed loop mode. In an embodiment, bipolar stimulation of the hypothalamus may be utilized with the following stimulation parameters: 130 Hz, 80 microsec pulse width and 2.5 Volts. In another embodiment, monopolar stimulation of the hypothalamus may be utilized with the following stimulation parameters: 50 Hz to 1000 Hz, 30 microseconds pulse width to 450 microseconds and 0.1 to 10 Volts.

Figure 2:
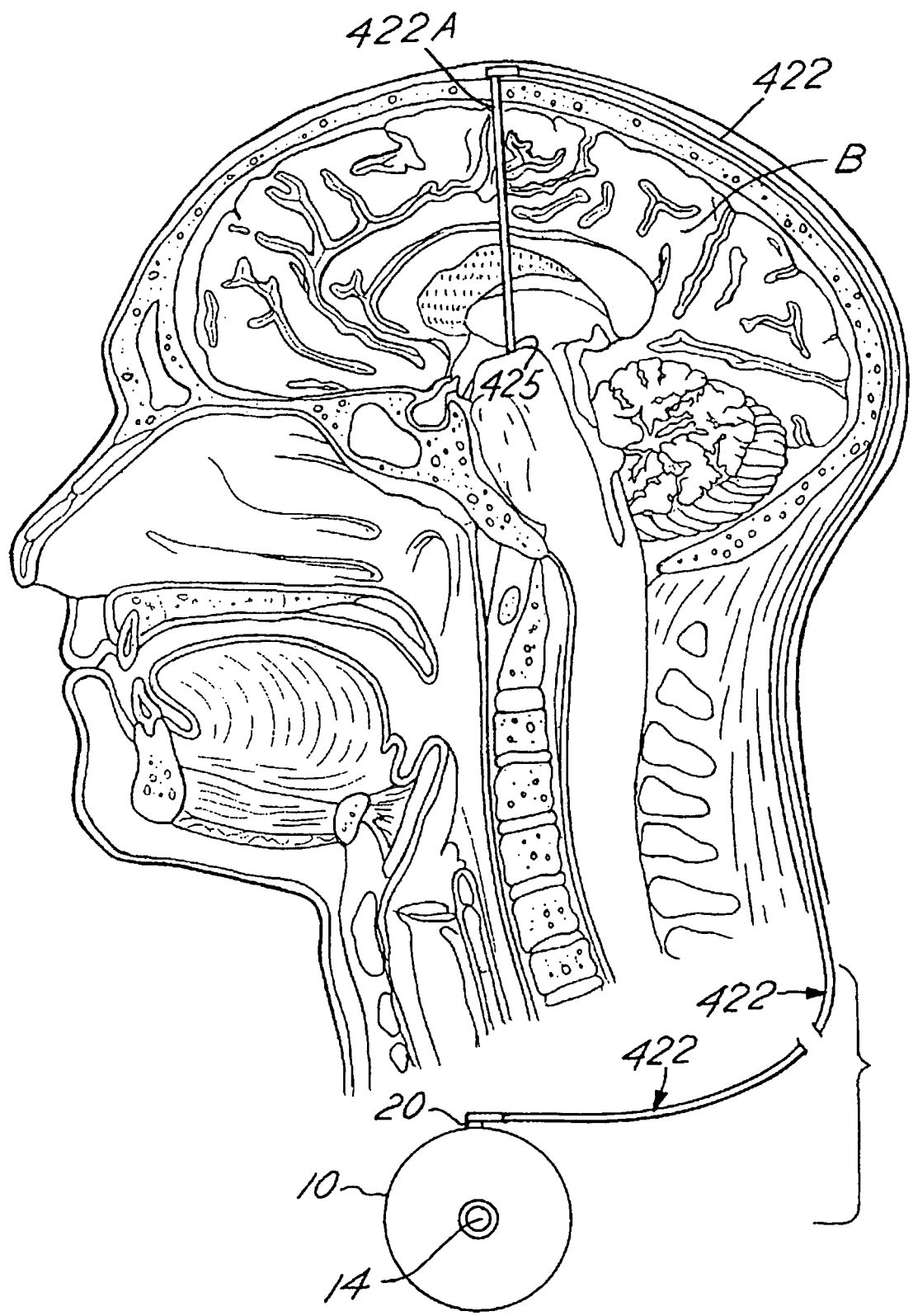
FIGS. 2 and 2A are diagrammatic illustrations of a catheter implanted in a brain according to an embodiment of the present invention.
Figure 2A:
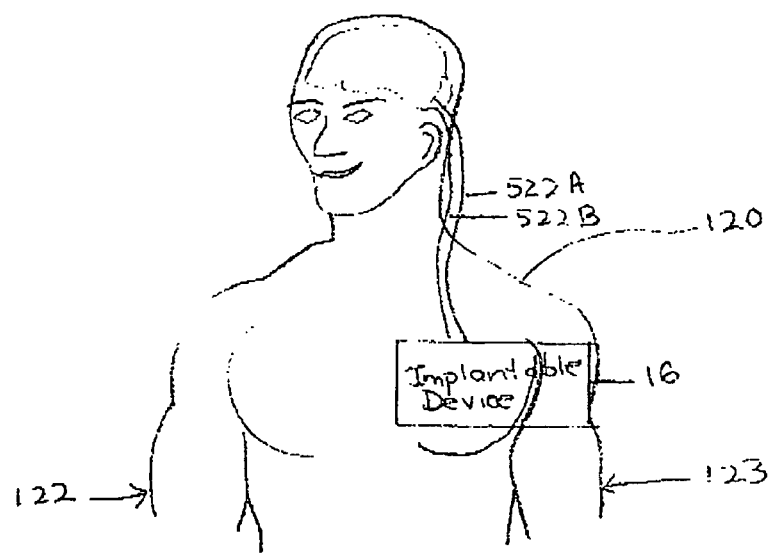

Referring to FIG. 2, in another embodiment, the system or device of the present invention may utilize drug delivery as the form of treatment therapy. A pump 10 may be implanted below the skin of a patient. The pump 10 has a port 14 into which a hypodermic needle can be inserted through the skin to inject a quantity of a liquid agent, such as a medication or drug. The liquid agent is delivered from pump 10 through a catheter port 20 into a catheter 422. Catheter 422 is positioned to deliver the agent to specific infusion sites in a brain (B). Pump 10 may take the form of any number of known implantable pumps including for example that which is disclosed in U.S. Pat. No. 4,692,147.

The distal end of catheter 422 terminates in a cylindrical hollow tube 422A having a distal end 425 implanted, by conventional stereotactic surgical techniques, into a portion of the brain to affect tissue within the human brain. Tube 422A is surgically implanted through a hole in the skull and catheter 422 is implanted between the skull and the scalp as shown in FIG. 2. Catheter 422 is joined to pump 10 in the manner shown. Pump 10 is implanted in a human body in a subcutaneous pocket located in the chest below the clavicle. Alternatively, pump 10 may be implanted in the abdomen.

Catheter 422 may be divided into twin tubes 422A and 422B (not shown) that are implanted into the brain bilaterally. Alternatively, tube 422B (not shown) implanted on the other side of the brain may be supplied with drugs from a separate catheter and pump.

The pump 10 may be programmed to deliver drug according to a particular dosage and/or time interval. For example, the pump may delivery drug therapy over a first period when the dose is higher to induce a high level of neurogenesis followed by a longer period of ongoing delivery to maintain neurogenesis and secondary trophic effects like axonal sprouting and synaptogenesis. Any number of neurotrophins or drugs that stimulate neurons may be administered including, but not limited to, NGF, BDNF, NT-3, FGF, EGF, GDNF, Neurteurin, Artemin, Persephin.

Alternatively, a combination of treatment therapies may be delivered to provide influencing of various neuronal types. For example, it may be desirable to concurrently influence, via drug and/or electrical stimulation, the neurons in the hippocampus and other portions of the brain to achieve an improved result. Such a device to utilize both forms of treatment therapy may be that which is disclosed, for example, in U.S. Pat. No. 5,782,798. In addition to affecting the deep brain, it may be desirable to affect concurrently other portions of the brain.

Figure 3:
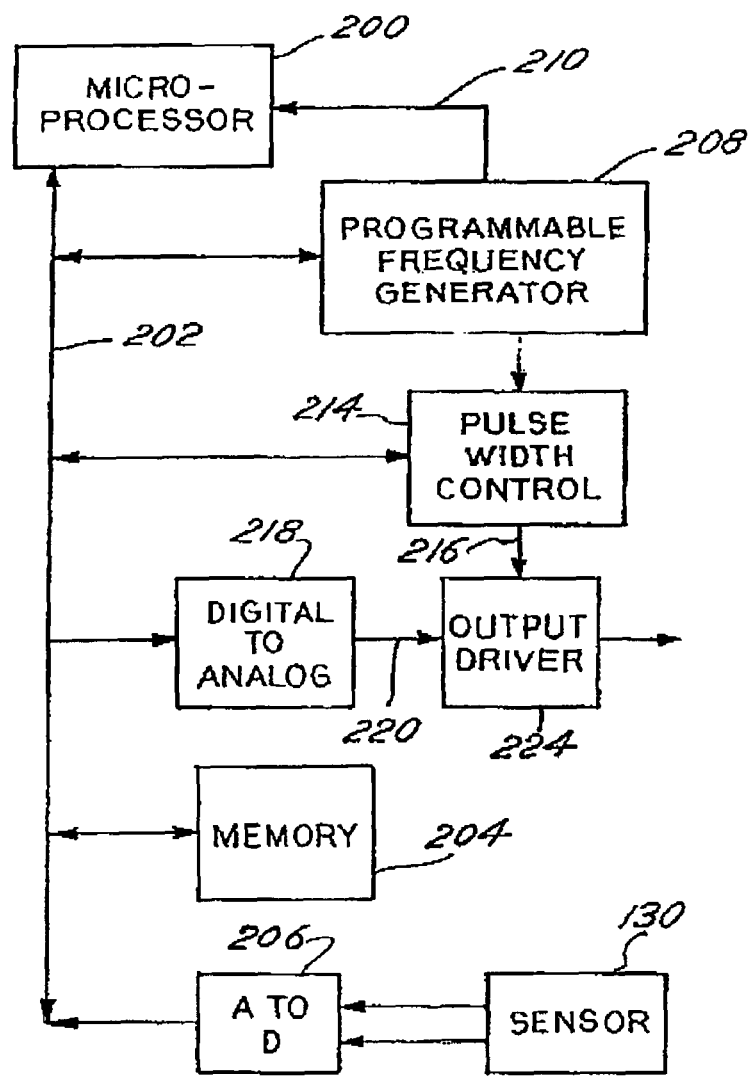
FIG. 3 is a schematic block diagram of a microprocessor and related circuitry of an implantable medical device for use with the present invention.

Referring to FIG. 3, the overall components of the implanted device 16 are shown (similar components may also be found for pump 10). The stimulus pulse frequency is controlled by programming a value to a programmable frequency generator 208 using bus 202. The programmable frequency generator provides an interrupt signal to microprocessor 200 through an interrupt line 210 when each stimulus pulse is to be generated. The frequency generator may be implemented by model CDP1878 sold by Harris Corporation. The amplitude for each stimulus pulse is programmed to a digital to analog converter 218 using bus 202. The analog output is conveyed through a conductor 220 to an output driver circuit 224 to control stimulus amplitude.

Microprocessor 200 also programs a pulse width control module 214 using bus 202. The pulse width control provides an enabling pulse of duration equal to the pulse width via a conductor 216. Pulses with the selected characteristics are then delivered from device 16 through cable 522 and lead 522A to the desired regions of the brain.

At the time the stimulation device 16 is implanted, the clinician programs certain key parameters into the memory of the implanted device via telemetry. These parameters may be updated subsequently as needed.

The embodiments of the present invention shown above are open-loop systems. The microcomputer algorithm programmed by the clinician sets the stimulation parameters of signal generator 16. This algorithm may change the parameter values over time but does so independent of any changes in symptoms the patient may be experiencing. Alternatively, a closed-loop system discussed below which incorporate a sensor 130 to provide feedback could be used to provide enhanced results. Sensor 130 can be used with a closed loop feedback system in order to automatically determine the level of electrical stimulation necessary to achieve the desired level of neurogenesis. In a closed-loop embodiment, microprocessor 200 executes a control algorithm in order to provide stimulation with closed loop feedback control. Such an algorithm may analyze a sensed signal and deliver the electrical for chemical treatment therapy based on the sensed signal falling within or outside predetermined values or windows, for example, for BDNF and other neurotrophins (e.g., NGF, CNTF, FGF EGF, NT-3) and corticosteroids.

The control algorithm may be operable on-line or in real time by detecting an electophysiological or chemical signal or off line by measuring a predetermined clinical benefit. Alternatively, the therapy could be guided by the goal of repopulating neurons up to a certain level. Such an increase in of neuronal number could be assessed using the techniques described below.

For example, the sensor may generate a sensor signal related to the extent of neuronal loss. In an embodiment, the extent of electrical activity or the levels of a neurochemical may be measured that are indicative of neuronal loss. For example magnetic resonance spectroscopy may be used to sense the N-acetylaspartate (NAA) to creatine (Cr) ratio (NAA/Cr) as an indicator of neuronal loss. Alternatively, the neuronal loss may be estimated by measuring the volume of the neural structure of interest, which may be achieved by Magnetic Resonance Imaging vollumetry. Any other techniques may also be used to sense the extent of neuronal loss including, for example, MR volumetry, DWI, magnetization transfer MR imaging, and 1H MRS and PET).

Figure 4B:
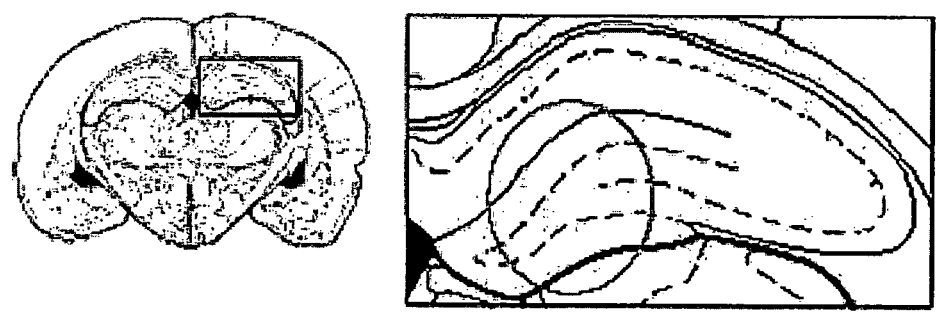

As another example, the sensing may provide an indication of a cognitive disorder. Thus, sensor 130 may be placed in the dentate gyrus (FIG. 4(b)) to confirm that stimulation at the anterior thalamic nuclei affects neuronal activity of the hippocampus. U.S. Pat. No. 6,227,203 provides examples of various types of sensors that may be used to detect a symptom or a condition of a cognitive disorder and responsively generate a neurological signal. In an embodiment, a neurochemical characteristic of the cognitive function may be sensed, additionally or alternatively. For example, sensing of local levels of neurotransmitters (glutamate, GABA, Aspartate), local pH or ion concentration, lactate levels, local cerebral blood flow, glucose utilization or oxygen extraction may also be used as the input component of a closed loop system. These measurements could be taken at rest or in response to a specific memory or cognitive task or in response to a specific sensory or motor stimulus. In another embodiment, an electro-physiological characteristic of the cognitive function may be sensed, for example, the frequency and pattern of discharge of individual neurons or the amplitude of a local electric field potential. The information contained within the neuronal firing spike train, including spike amplitude, frequency of action potentials, signal to noise ratio, the spatial and temporal features and the pattern of neuronal firing, oscillation behavior and inter-neuronal correlated activity could be used to deliver therapies on a contingency basis in a closed loop system. Moreover, treatment therapy delivered may be immediate or delayed, diurnal, constant or intermittent depending on contingencies as defined by the closed loop system.

In one embodiment, the system may provide continuous closed-loop feedback control. In another embodiment, the system may be switchable between open-loop and closed-loop by operator control.

Referring back to FIG. 3, the system may optionally utilize closed-loop feedback control having an analog to digital converter 206 coupled to sensor 130. Output of the A-to-D converter 206 is connected to microprocessor 200 through peripheral bus 202 including address, data and control lines. Microprocessor 200 processes sensor data in different ways depending on the type of transducer in use and regulates delivery, via a control algorithm, of electrical stimulation and/or drug delivery based on the sensed signal. For example, when the signal on sensor 130 exceeds a level programmed by the clinician and stored in a memory 204, increasing amounts of treatment therapy may be applied through an output driver 224. In the case of electrical stimulation, a parameter of the stimulation may be adjusted such as amplitude, pulse width and/or frequency.

In another aspect of the invention, treatment therapy may be utilized to also improve cognitive function. Techniques for improving cognitive function through treatment therapy are disclosed in a co-pending patent application entitled "Improving Cognitive Function Within A Human Brain," filed concurrent with the instant application and incorporated herein by reference in its entirety.

Thus, embodiments of INDUCING NEUROGENESIS WITHIN A HUMAN BRAIN are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:

1. A method for inducing neurogenesis in a brain of a human to treat Alzheimer's Disease or mild cognitive impairment (MCI) by means of an implantable signal generator and a lead having a proximal end coupled to the signal generator and a distal portion having at least one electrode, the method comprising:
   A) selecting a patient suffering from Alzheimer's Disease or mild cognitive impairment (MCI);
   implanting the at least one electrode in an anterior thalamic nuclei complex of the Papez circuit of the patient;
   C) coupling the proximal end of the implanted electrode to the sign generator; and
   D) operating the signal generator to deliver high frequency stimulation of about 50 to about 200 Hz to the anterior thalamic nuclei complex to cause a production of new or replacement neurons in a second portion of the Papez circuit, including at least a hippocampus.

2. A method, as claimed in claim 1, wherein D) comprises selecting amplitude, width and frequency of stimulation by the electrode.

3. A method, as claimed in claim 1, wherein D) comprises operating the signal generator to pulse at a pulse amplitude between 0.1 Volts to 10.0 Volts.

4. A method, as claimed in claim 1, wherein D) comprises operating the signal generator to pulse at a pulse width between 30 microseconds and 450 microseconds.

5. A method, as claimed in claim 1, wherein D) comprises operating the signal generator in a monopolar configuration.

6. A method, as claimed in claim 1, wherein D) comprises operating the signal generator in a bipolar configuration.

7. A method, as claimed in claim 1, wherein D) comprises operating, the signal generator in a multipolar configuration.

8. A method, as claimed in claim 1, wherein D) comprises operating the signal generator in a continuous mode.

9. A method, as claimed in claim 1, wherein D) comprises operating the signal generator in a cyclical mode.

10. A method, as claimed in claim 1, further comprising E) selecting between an open loop and a closed loop mode of operation.

11. A method as claimed in claim 1, further comprising:
   E) sensing a characteristic indicative of an extent of neurogenesis and generating a sensor signal; and
   F) regulating the operation of the signal generator in response to the sensor signal.

12. A method, as claimed in claim 11, wherein E) comprises detecting a neurochemical characteristic of the neurogenesis.

13. A method, as claimed in claim 11, wherein E) comprises detecting an electro-physiological characteristic of the neurogenesis.

14. A method as claimed in claim 11, wherein F) comprises executing, a control algorithm.

15. A method, as claimed in claim 11, wherein F) comprises adjusting at least one parameter of the stimulation, the parameter being selected from the group consisting of amplitude, pulse width and frequency.

16. A method, as claimed in claim 1, further comprising:
   E) implanting at least one secondary electrode in communication with a deep brain tissue element;
   F) coupling the secondary electrode to the signal generator; and
   G) operating the signal generator to stimulate the deep brain tissue element.

17. A method, as claimed in claim 1, further comprising:
   E) implanting at least one catheter so that a discharge portion lies in communication with a deep brain tissue element;
   F) coupling the catheter to a pump; and
   G) operating the pump to deliver drug, to the deep brain tissue element.

18. The method of claim 1, wherein the second portion of the Papez circuit comprises a dentate gyros which includes the hippocampus.

* * * * *

UNITED STATES PATENT AND TRADEMARK OFFICE
CERTIFICATE OF CORRECTION

| | | |
|---|---|---|
| PATENT NO. | : 8,612,006 B2 | Page 1 of 1 |
| APPLICATION NO. | : 11/303292 | |
| DATED | : December 17, 2013 | |
| INVENTOR(S) | : Lozano et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 220 days.

Signed and Sealed this
Twenty-fifth Day of August, 2015

Michelle K. Lee
*Director of the United States Patent and Trademark Office*